(12) United States Patent
Deyanov et al.

(10) Patent No.: US 12,137,874 B2
(45) Date of Patent: Nov. 12, 2024

(54) CONNECTOR ASSEMBLY WITH A RADIO FREQUENCY COMMUNICATION DEVICE AND WITH AN INDUCTION COIL FOR A SURGICAL INSTRUMENT AND A CORRESPONDING RECEIVER ASSEMBLY

(71) Applicant: Intuitive Surgical Operations, Inc., Sunnyvale, CA (US)

(72) Inventors: Rumen Deyanov, Fremont, CA (US); Jonathan D. Halderman, Sunnyvale, CA (US); Derek C. Liou, Cupertino, CA (US); Kierstin Gray Parrish, Boulder Creek, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 614 days.

(21) Appl. No.: 17/421,861

(22) PCT Filed: Jan. 15, 2020

(86) PCT No.: PCT/US2020/013699
§ 371 (c)(1),
(2) Date: Jul. 9, 2021

(87) PCT Pub. No.: WO2020/150365
PCT Pub. Date: Jul. 23, 2020

(65) Prior Publication Data
US 2022/0104692 A1    Apr. 7, 2022

Related U.S. Application Data

(60) Provisional application No. 62/794,554, filed on Jan. 18, 2019.

(51) Int. Cl.
*A61B 1/00*    (2006.01)

(52) U.S. Cl.
CPC ...... *A61B 1/00124* (2013.01); *A61B 1/00016* (2013.01); *A61B 1/00126* (2013.01)

(58) Field of Classification Search
CPC ............ A61B 1/00124; A61B 1/00016; A61B 1/00126; A61B 1/00112; A61B 1/00114;
(Continued)

(56) References Cited

U.S. PATENT DOCUMENTS 6,293,910 B1 * 9/2001 Yamakita ............. A61B 1/0623
                                                            600/110
6,458,078 B1 * 10/2002 Ludtke ..................... A61B 1/05
                                                          348/E5.029

(Continued)

OTHER PUBLICATIONS

International Preliminary Report on Patentability for Application No. PCT/US2020/013699, mailed on Jul. 29, 2021, 13 pages.

(Continued)

*Primary Examiner* — Timothy J Neal
*Assistant Examiner* — James Edward Boice

(57) ABSTRACT

An exemplary connection system includes a connector assembly and a receiver assembly. The connector assembly includes a hermetically-sealed housing, a first RF communication device within the housing and communicatively coupled to a surgical instrument and a first induction coil within the housing and electrically coupled to the surgical instrument. The receiver assembly includes a second RF communication device communicatively coupled to a controller of the surgical instrument, a second induction coil electrically coupled to a power source and a receptacle configured to receive the connector assembly such that the first RF communication device is aligned with the second RF communication device, the first induction coil is aligned with the second induction coil, the first RF communication device may wirelessly communicate with the second RF communication device, and the second induction coil may (Continued)

inductively couple to the first induction coil to wirelessly transmit power to the first induction coil.

16 Claims, 8 Drawing Sheets

(58) Field of Classification Search
CPC ............ A61B 1/00117; A61B 1/00121; A61B 1/00128; A61B 1/00029; A61B 1/00193; A61B 1/121; G01N 29/2481
USPC .................................................. 600/109, 132
See application file for complete search history.

(56) References Cited

U.S. PATENT DOCUMENTS

| 6,503,196 | B1* | 1/2003 | Kehr | .................. | A61B 1/00135 |
| | | | | | 600/176 |
| 2007/0060789 | A1 | 3/2007 | Uchimura et al. | | |
| 2010/0326703 | A1* | 12/2010 | Gilad | ..................... | A61B 1/041 |
| | | | | | 174/254 |
| 2012/0262560 | A1* | 10/2012 | Nisani | .................... | A61B 1/041 |
| | | | | | 348/E7.085 |
| 2016/0089000 | A1 | 3/2016 | Hara | | |
| 2016/0094051 | A1* | 3/2016 | Soar | ..................... | H04B 5/0037 |
| | | | | | 307/9.1 |
| 2016/0128550 | A1 | 5/2016 | Laser et al. | | |
| 2017/0112354 | A1* | 4/2017 | DiCarlo | ................. | H04N 23/10 |
| 2018/0296067 | A1 | 10/2018 | Amling et al. | | |
| 2019/0159666 | A1* | 5/2019 | Matlock | ................ | A61M 25/09 |

OTHER PUBLICATIONS

International Search Report and Written Opinion for Application No. PCT/US2020/013699, mailed on Jun. 24, 2020, 20 pages.
Invitation to pay additional fee received from the International Search Authority for PCT/US2020/013699, mailed Apr. 1, 2020, 15 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

CONNECTOR ASSEMBLY WITH A RADIO FREQUENCY COMMUNICATION DEVICE AND WITH AN INDUCTION COIL FOR A SURGICAL INSTRUMENT AND A CORRESPONDING RECEIVER ASSEMBLY

RELATED APPLICATIONS

The present application is a U.S. National Stage Application under 35 U.S.C. § 371 of International Application No. PCT/US2020/013699, filed on Jan. 15, 2020, which claims priority to U.S. Provisional Patent Application No. 62/794,554, filed on Jan. 18, 2019, the contents of which are hereby incorporated by reference in their entirety.

BACKGROUND INFORMATION

During a surgical procedure performed with a computer-assisted surgical system, a surgical instrument may be connected to a computing system by a cable. For example, a connector at the end of the cable may be plugged into a receptacle of the computing system. The connector typically has metal contacts that conductively couple to corresponding metal contacts of the receptacle. In this configuration, data generated by the surgical instrument may be transmitted, by way of the cable, to the computing system for use during the surgical procedure, and the computing system may provide control signals and/or power to the surgical instrument by way of the cable. As an example, an endoscope may capture images of a surgical area within a patient and transmit image data representative of the captured images to a computing system, which may process and display the captured images. The computing device may also provide power to the endoscope by way of the cable, and may control operation of image sensors included in the endoscope by transmitting control signals to the endoscope by way of the cable.

After the surgical procedure, the surgical instrument and cable are cleaned and sterilized, such as by an autoclave or a low temperature sterilization process. However, such sterilization processes may degrade the metal contacts on the connector of the cable, which may result in a faulty connection between the surgical instrument and the computing system.

SUMMARY

An exemplary connection system may include a connector assembly and a receiver assembly. The connector assembly may include a hermetically-sealed housing, a first radio frequency ("RF") communication device disposed within the housing and communicatively coupled to a surgical instrument, and a first induction coil disposed within the housing and electrically coupled to the surgical instrument. The receiver assembly may include a second RF communication device communicatively coupled to a controller of the surgical instrument, a second induction coil electrically coupled to a power source, and a receptacle configured to receive the connector assembly such that, while the connector assembly is positioned in the receptacle, the first RF communication device is aligned with the second RF communication device and the first induction coil is aligned with the second induction coil. While the connector assembly is positioned in the receptacle, the first RF communication device may be configured to wirelessly communicate with the second RF communication device, and the second induction coil may be configured to inductively couple to the first induction coil to wirelessly transmit power to the surgical instrument by way of the first induction coil.

An exemplary connector assembly includes a hermetically-sealed housing, a first RF communication device disposed within the housing and communicatively coupled to a surgical instrument, and a first induction coil electrically coupled to the surgical instrument. The connector assembly is configured to be positioned in a receptacle of a receiver assembly such that, while the connector assembly is positioned in the receptacle, the first RF communication device is aligned with a second RF communication device included in the receiver assembly and the first induction coil is aligned with a second induction coil included in the receiver assembly, the second induction coil being electrically coupled to a power source. While the connector assembly is positioned in the receptacle, the first RF communication device is configured to wirelessly communicate with the second RF communication device, and the second induction coil is configured to inductively couple to the first induction coil to wirelessly transmit power to the surgical instrument by way of the first induction coil.

An exemplary receiver assembly includes a receptacle configured to receive a connector assembly that includes a first RF communication device communicatively coupled to a surgical instrument and a first induction coil electrically coupled to the surgical instrument, a second RF communication device communicatively coupled to a controller of the surgical instrument, and a second induction coil electrically coupled to a power source. While the connector assembly is positioned in the receptacle, the second RF communication device is aligned with the first RF communication device such that the second RF communication device is configured to wirelessly communicate with the first RF communication device, and the second induction coil is aligned with the first induction coil such that the second induction coil is configured to inductively couple to the first induction coil to wirelessly transmit power to the surgical instrument by way of the first induction coil.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
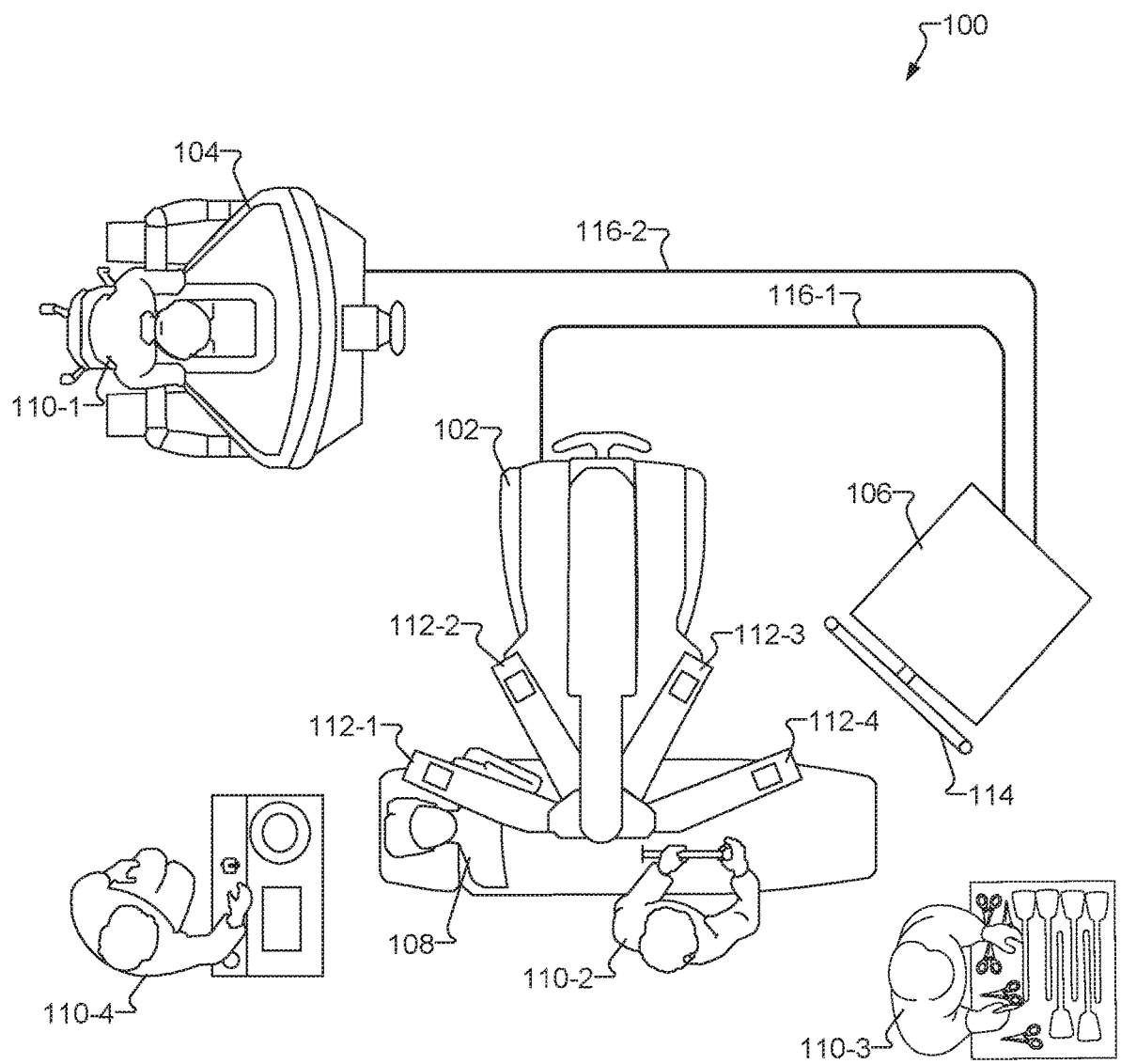
FIG. 1 illustrates an exemplary computer-assisted surgical system according to principles described herein.

Connection systems and apparatuses for a surgical instrument are described herein. As will be explained in more detail below, an exemplary connection system may include a connector assembly and a receiver assembly. The connector assembly includes a hermetically-sealed housing, a first RF communication device disposed within the housing and communicatively coupled to a surgical instrument, and a first induction coil disposed within the housing and electrically coupled to the surgical instrument. The receiver assembly includes a second RF communication device communicatively coupled to a controller of the surgical instrument, a second induction coil electrically coupled to a power source, and a receptacle configured to receive the connector assembly such that, while the connector assembly is positioned in the receptacle, the first RF communication device is aligned with the second RF communication device and the first induction coil is aligned with the second induction coil. While the connector assembly is positioned in the receptacle, the first RF communication device is configured to wirelessly communicate with the second RF communication device, and the second induction coil is configured to inductively couple to the first induction coil to wirelessly transmit power to the surgical instrument by way of the first induction coil.

In some examples, the connector assembly may further include a first light guide disposed within the housing and optically coupled to the surgical instrument, and the receiver assembly may further include a second light guide optically coupled to an illumination source configured to emit light. While the connector assembly is positioned in the receptacle, the first light guide is optically aligned with the second light guide such that the light emitted from the illumination source is conveyed to the surgical instrument by way of the second light guide and the first light guide.

Various benefits may be provided by the connection systems and apparatuses described herein. For example, the connection systems and apparatuses described herein enable high-speed transmission of data between a surgical instrument and a controller of the surgical instrument and delivery of power to the surgical instrument, all without making conductive contact between the connector assembly and the receiver assembly. Accordingly, the connector assembly can be easily sterilized after use without degrading any of the components of the connector assembly, and hence without degrading the communication and power connections.

Additionally, the connection systems and apparatuses described herein may help reduce the risk of inadvertent capacitive coupling discharge by a surgical instrument positioned within a surgical area associated with a patient. For example, by using a connection system as described herein, a conductive path between the surgical instrument and a computing system may be avoided, thereby isolating the surgical instrument from the computing system and preventing electrical current from being capacitively coupled onto the surgical instrument.

Various embodiments will now be described in more detail with reference to the figures. The systems and methods described herein may provide one or more of the benefits mentioned above and/or various additional and/or alternative benefits that will be made apparent herein.

The connection systems and apparatuses described herein may be implemented as part of or in conjunction with a computer-assisted surgical system. As such, an exemplary computer-assisted surgical system will now be described. The following exemplary computer-assisted surgical system is illustrative and not limiting, as the connection systems and apparatuses described herein may be implemented as part of or in conjunction with other suitable surgical systems.

FIG. 1 illustrates an exemplary computer-assisted surgical system 100 ("surgical system 100"). As shown, surgical system 100 may include a manipulating system 102, a user control system 104, and an auxiliary system 106 communicatively coupled one to another.

Surgical system 100 may be utilized by a surgical team to perform a computer-assisted surgical procedure on a patient 108. As shown, the surgical team may include a surgeon 110-1, an assistant 110-2, a nurse 110-3, and an anesthesiologist 110-4, all of whom may be collectively referred to as "surgical team members 110," Additional or alternative surgical team members may be present during a surgical session as may serve a particular implementation.

While FIG. 1 illustrates an ongoing minimally invasive surgical procedure, surgical system 100 may similarly be used to perform open surgical procedures or other types of surgical procedures that may similarly benefit from the accuracy and convenience of surgical system 100. Additionally, it will be understood that the surgical session throughout which surgical system 100 may be employed may not only include an operative phase of a surgical procedure, as is illustrated in FIG. 1, but may also include preoperative, postoperative, and/or other suitable phases of the surgical procedure, A surgical procedure may include any procedure in which manual and/or instrumental techniques are used on a patient to investigate, diagnose, or treat a physical condition of the patient. Additionally, a surgical procedure may include any procedure that is not performed on a live patient, such as a calibration procedure, a training procedure, and an experimental or research procedure.

As shown in FIG. 1, manipulating system 102 may include a plurality of manipulator arms 112 (e.g., manipulator arms 112-1 through 112-4) to which a plurality of surgical instruments (not shown) may be coupled, Each surgical instrument may be implemented by any suitable surgical tool (e.g., a tool having tissue-interaction functions), medical tool, monitoring instrument (e.g., an endoscope), sensing instrument (e.g., a force-sensing surgical instrument), diagnostic instrument, or the like that may be used for a computer-assisted surgical procedure (e.g., by being at least partially inserted into patient 108 and manipulated to perform a computer-assisted surgical procedure on patient 108). While manipulating system 102 is depicted and described herein as including four manipulator arms 112, it will be recognized that manipulating system 102 may include only a single manipulator arm 112 or any other number of manipulator arms as may serve a particular implementation.

Manipulator arms 112 and/or surgical instruments attached to manipulator arms 112 may include one or more displacement transducers, orientational sensors, and/or positional sensors used to generate raw (i.e., uncorrected) kinematics information (hereinafter "surgical system sensors"). One or more components of surgical system 100 may be configured to use the kinematics information to track (e.g., determine positions of) and/or control the surgical instruments.

Surgical instruments attached to manipulator arms 112 may each be positioned at a surgical area associated with a patient. A "surgical area" may, in certain examples, be entirely disposed within a patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments being used to perform the surgical procedure are located. In other examples, a surgical area may be at least partially disposed external to the patient at or near where a surgical procedure is planned to be performed, is being performed, or has been performed on the patient. For instance, surgical system 100 may be used to perform an open surgical procedure such that part of the surgical area (e.g., tissue being operated on) is internal to the patient while another part of the surgical area (e.g., a space around the tissue where one or more surgical instruments may be disposed) is external to the patient. A surgical instrument may be referred to as being positioned or located at or within a surgical area when at least a portion of the surgical instrument (e.g., a distal portion of the surgical instrument) is located within the surgical area.

User control system 104 may be configured to facilitate control by surgeon 110-1 of manipulator arms 112 and surgical instruments attached to manipulator arms 112. For example, surgeon 110-1 may interact with user control system 104 to remotely move or manipulate manipulator arms 112 and the surgical instruments. To this end, user control system 104 may provide surgeon 110-1 with imagery (e.g., high-definition 3D imagery) of a surgical area associated with patient 108 as captured by an imaging device (e.g., an endoscope). In certain examples, user control system 104 may include a stereo viewer having two displays where stereoscopic images of a surgical area associated with patient 108 and generated by a stereoscopic imaging system may be viewed by surgeon 110-1. Surgeon 110-1 may utilize the imagery to perform one or more procedures with one or more surgical instruments attached to manipulator arms 112.

To facilitate control of surgical instruments, user control system 104 may include a set of master controls (not shown). These master controls may be manipulated by surgeon 110-1 to control movement of surgical instruments (e.g., by utilizing robotic and/or teleoperation technology). The master controls may be configured to detect a wide variety of hand, wrist, and finger movements by surgeon 110-1. Based on the user manipulation of the master controls, control signals may be generated and transmitted to manipulator arms 112 and/or surgical instruments attached to manipulator arms 112 to control movement or operation of the manipulator arms 112 and/or surgical instruments. In this manner, surgeon 110-1 may intuitively perform a surgical procedure using one or more surgical instruments.

User control system 104 may further be configured to facilitate control by surgeon 110-1 of other components of surgical system 100. For example, surgeon 110-1 may interact with user control system 104 to change a configuration or operating mode of surgical system 100, to change a display mode of surgical system 100, to generate additional control signals used to control surgical instruments attached to manipulator arms 112, to facilitate switching control from one surgical instrument to another, or to perform any other suitable operation. To this end, user control system 104 may also include one or more input devices (e.g., foot pedals, buttons, switches, etc.) configured to receive input from surgeon 110-1.

Auxiliary system 106 may include one or more computing devices configured to perform primary processing operations of surgical system 100. The one or more computing devices included in auxiliary system 106 may control and/or coordinate operations performed by various other components (e.g., manipulating system 102, surgical instruments attached to manipulator arms 112, and/or user control system 104) of surgical system 100. For example, a surgical instrument controller may receive and/or generate control signals and transmit the control signals to manipulating system 102 (e.g., to a surgical instrument attached to a manipulator arm 112), As another example, auxiliary system 106 (e.g., the surgical instrument controller) may receive and process image data representative of imagery captured by an imaging device (e.g., an endoscope) attached to a manipulator arm 112 and transmit the image data to user control system 104 for display on a display device (e.g., a stereo viewer) included in user control system 104.

In some examples, auxiliary system 106 may be configured to present visual content to surgical team members 110 who may not have access to the images provided to surgeon 110-1 at user control system 104. To this end, auxiliary system 106 may include a display monitor 114 configured to display one or more user interfaces, such as images (e.g., 2D images) of the surgical area, information associated with patient 108 and/or the surgical procedure, and/or any other visual content as may serve a particular implementation. For example, display monitor 114 may display images of the surgical area together with additional content (e.g., graphical content, contextual information, etc.) concurrently displayed with the images. In some embodiments, display monitor 114 is implemented by a touchscreen display with which surgical team members 110 may interact (e.g., by way of touch gestures) to provide user input to surgical system 100.

In some examples, auxiliary system 106 (e.g., a surgical instrument controller) may include one or more power sources configured to provide electrical power to surgical instruments attached to manipulator arms 112. In additional examples, auxiliary system 106 (e.g., the surgical instrument controller) may include one or more illumination sources configured to emit light and convey the emitted light to a surgical instrument (e.g., an endoscope) attached to a manipulator arm.

Manipulating system 102, user control system 104, and auxiliary system 106 may be communicatively coupled one to another in any suitable manner. For example, as shown in FIG. 1, manipulating system 102 and auxiliary system 106 may be communicatively coupled by way of control line 116-1, and auxiliary system 106 and user control system 104 may be communicatively coupled by way of control line 116-2. Control line 116-1 may represent, for example, one or more cables connected to manipulating system 102 and/or surgical instruments attached to manipulator arms 112. Such cables may include, for example, one or more wired communication lines, power lines, optical fibers, and/or light guides. Control line 116-2 may represent any wired or wireless communication link as may serve a particular implementation. Manipulating system 102, user control system 104, and auxiliary system 106 may each include one or more wired or wireless communication interfaces, such as one or more connection systems, local area network interfaces, Wi-Fi network interfaces, cellular interfaces, etc.

Exemplary connection systems for communicatively, electrically, and/or optically coupling a surgical instrument to a controller of the surgical instrument (e.g., a controller included in user control system 104 or in auxiliary system 106) will be described below in more detail. In some examples, the surgical instrument may be implemented by an imaging device (e.g., a stereoscopic endoscope). Accordingly, an exemplary imaging system and imaging device will now be described. The following exemplary imaging system and imaging device are illustrative and not limiting, as the connection systems and apparatuses described herein may be implemented as part of or in conjunction with other suitable surgical instruments (e.g., a cautery instrument, a needle driver, a scissors-type instrument, a stapler, etc.).

Figure 2:
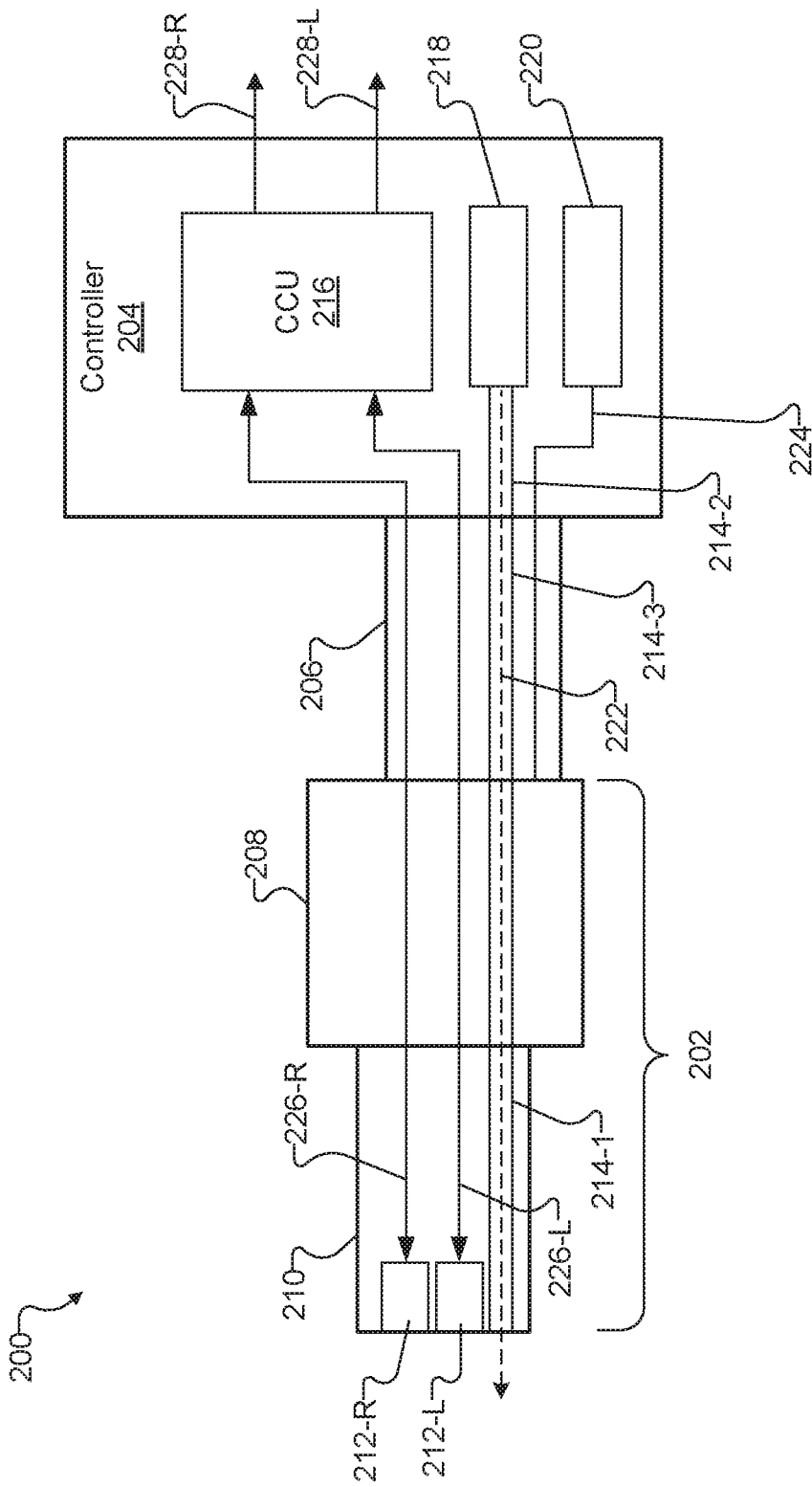
FIG. 2 illustrates a functional diagram of an exemplary imaging system that may be used in accordance with connection systems according to principles described herein.

FIG. 2 illustrates a functional diagram of an exemplary imaging system 200 that may be used in accordance with the connection systems and apparatuses described herein to capture images of a scene (e.g., a surgical area associated with patient 108). As shown, imaging system 200 includes an imaging device 202, a controller 204, and a cable 206 that interconnects imaging device 202 and controller 204. Imaging system 200 may include additional or alternative components as may serve a particular implementation. For example, imaging system 200 may include various optical and/or electrical signal transmission components (e.g., wires, lenses, optical fibers, choke circuits, waveguides, etc.).

Imaging device 202 may be implemented by an endoscope or other camera device configured to capture images of a scene. As shown, imaging device 202 includes a camera head 208, a shaft 210 coupled to and extending away from camera head 208, image sensors 212 (e.g., a right-side image sensor 212-R and a left-side image sensor 212-L) at a distal end of shaft 210, and a first illumination channel 214-1. In the example of FIG. 2, imaging device 202 is stereoscopic. Alternatively, in other examples imaging device 202 may be monoscopic (e.g., by including one image sensor 212 instead of two image sensors 212).

Imaging device 202 may be manually handled and controlled (e.g., by a surgeon performing a surgical procedure on a patient). Alternatively, camera head 208 may be coupled to a manipulator arm (e.g., one of manipulator arms 112) of a computer-assisted surgical system (e.g., surgical system 100) and imaging device 202 may be controlled using robotic and/or teleoperation technology.

The distal end of shaft 210 may be positioned at or near a scene that is to be imaged by imaging device 202. For example, the distal end of shaft 210 may be inserted into a patient. In this configuration, imaging device 202 may be used to capture images of anatomy and/or other objects within the scene.

Image sensors 212 may each be implemented by any suitable image sensor, such as a charge coupled device ("CCD") image sensor, a complementary metal-oxide semiconductor ("CMOS") image sensor, or the like. In some examples, as shown in FIG. 2, image sensors 212 are positioned at the distal end of shaft 210. Alternatively, image sensors 212 may be positioned closer to a proximal end of shaft 210, inside camera head 208, or outside imaging device 202 (e.g., inside controller 204). In these alternative configurations, optics (e.g., lenses, optical fibers, etc.) included in shaft 210 and/or camera head 208 may convey light from a scene to image sensors 212.

Image sensors 212 are configured to detect (e.g., capture, collect, sense, or otherwise acquire) light. For example, image sensor 212-R is configured to detect the light from a right-side perspective, and image sensor 212-L is configured to detect the light from a left-side perspective. The light detected by image sensors 212 may include, for example, visible light reflected by an object included within the scene and/or fluorescence illumination emitted by a fluorescence imaging agent (e.g., a fluorescent dye, a fluorophore, or a fluorescent protein that has been injected or absorbed into a bloodstream of a patient) within the scene. As will be illustrated below, image sensors 212 may convert the detected light into data representative of one or more images.

First illumination channel 214-1 may be implemented by one or more optical components (e.g., optical fibers, light guides, lenses, etc.). As will be described below, illumination may be provided to the scene by way of first illumination channel 214-1 in imaging device 202 to illuminate a scene.

Controller 204 may be implemented by any suitable combination of hardware and software configured to control and/or interface with imaging device 202. For example, controller 204 may be at least partially implemented by a computing device included in auxiliary system 106. Controller 204 includes a camera control unit ("CCU") 216, an illumination source 218, and a power source 220. Controller 204 may include additional or alternative components as may serve a particular implementation. In some examples, CCU 216 and/or illumination source 218 are alternatively included in imaging device 202 (e.g., in camera head 208).

CCU 216 is configured to control various parameters (e.g., activation times, auto exposure, etc.) of image sensors 212. To this end, CCU 216 may be configured to receive and/or generate control signals and transmit the control signals to imaging device 202 (e.g., image sensors 212). As will be described below, CCU 216 may be further configured to receive and process image data from image sensors 212. While CCU 216 is shown in FIG. 2 to be a single unit, CCU 216 may alternatively be implemented by a first CCU configured to control image sensor 212-R and a second CCU configured to control image sensor 212-L.

Illumination source 218 may be configured to generate and emit illumination 222. Illumination 222 (which is also referred herein to as light) may travel by way of a second illumination channel 214-2 included in controller 204 and a third illumination channel 214-3 included in cable 206. At imaging device 202, illumination 222 travels by way of first illumination channel 214-1 to a distal end of shaft 210, where illumination 222 exits to illuminate a scene. Together, first illumination channel 214-1, second illumination channel 214-2, and third illumination channel 214-3 may be referred to herein as illumination channel 214. While illumination source 218 is shown to be a single device in controller 204, illumination source 218 may alternatively include multiple illumination sources each configured to generate and emit differently configured illumination. Additionally, while illumination channel 214 is shown to be a single channel, illumination channel 214 may include multiple different optics (e.g., lenses, optical fibers, waveguides, etc.).

Power source 220 may include circuitry configured to provide electrical power to components included in imaging device 202. Electrical power may be transmitted to imaging device 202 by way of power wiring 224 included in cable 206.

To capture one or more images of a scene, controller 204 (or any other suitable computing device) may activate illumination source 218 and image sensors 212. While activated, illumination source 218 emits illumination 222, which travels via illumination channel 214 to the scene. Image sensors 212 detect illumination reflected from one or more surfaces in the scene. Image sensors 212 (and/or other circuitry included in imaging device 202) may convert the detected light into image data 226 representative of one or more images of the scene. For example, image sensor 212-R outputs image data 226-R representative of images captured from a right-side perspective and image sensor 212-L outputs image data 226-L representative of images captured from a left-side perspective. Image data 226 may have any suitable format.

Image data 226 is transmitted from image sensors 212 to CCU 216. Image data 226 may be transmitted by way of any suitable communication link between image sensors 212 and CCU 216. For example, image data 226 may be transmitted to CCU 216 by way of one or more wires included in cable 206. Additionally or alternatively, image data 226 may be transmitted to CCU 216 by way of one or more optical fibers.

CCU 216 may process (e.g., packetize and/or format) image data 226 and output processed image data 228 (e.g., processed image data 228-R corresponding to image data 226-R and processed image data 228-L corresponding to image data 226-L).

Processed image data 228 may be transmitted to an image processor (not shown) for further processing. The image processor may be implemented by one or more computing devices external to imaging system 200, such as one or more computing devices included in surgical system 100 (e.g., in one or more computing devices included within auxiliary system 106). In some examples, the image processor is implemented by a processing facility of surgical system 100. Alternatively, the image processor may be included in controller 204. The image processor may prepare processed image data 228 for display, in the form of one or more still images and/or video content, on one or more display devices (e.g., a stereo viewer of user control system 104 or display monitor 114 of auxiliary system 106).

As mentioned, cable 206 may include one or more communication channels (e.g., wires and/or optical fibers) for transmitting data (e.g., image data 226 and/or control signals) between imaging device 202 and controller 204, a power transmission channel (e.g., one or more power wires) for transmitting electrical power from power source 220 to imaging device 202, and an illumination channel for conveying illumination 222 from illumination source 218 to imaging device 202. Cable 206 may be removably connected to controller 204, thereby enabling cable 206 to be removed from controller 204, such as for cleaning and sterilizing imaging device 202 and cable 206 and/or swapping instruments.

Exemplary connection systems and apparatuses for communicatively, electrically, and/or optically connecting a surgical instrument (e.g., imaging device 202) with a controller of the surgical instrument (e.g., controller 204) will now be described. The following description is merely illustrative and is not limiting.

Figure 3:
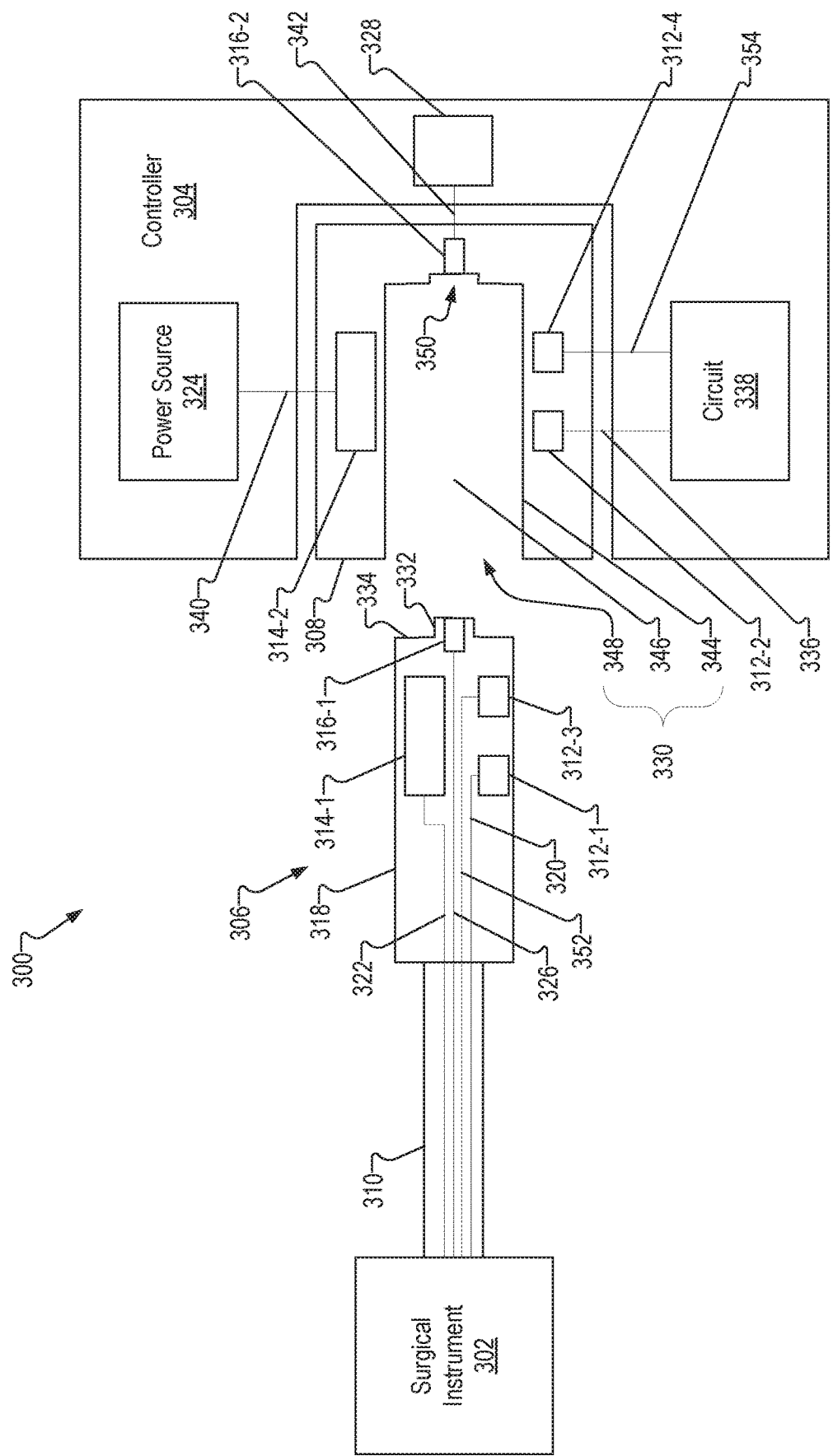
FIG. 3 illustrates a functional diagram of an exemplary connection system according to principles described herein.

FIG. 3 illustrates a functional diagram of an exemplary connection system 300 that may be used in accordance with the systems and methods described herein to connect a surgical instrument 302 (e.g., imaging device 202) with a controller 304 of surgical instrument 302 (e.g., controller 204). As shown, connection system 300 includes a connector assembly 306 and a receiver assembly 308. Connector assembly 306 is coupled (e.g., communicatively, electrically, and optically) with surgical instrument 302, and receiver assembly 308 is coupled (e.g., communicatively, electrically, and optically) with controller 304 and configured to receive connector assembly 306.

As shown, connector assembly 306 is positioned at a proximal end of a cable 310 (e.g., cable 206), and a distal end of cable 310 is coupled to surgical instrument 302. Alternatively, connector assembly 306 may be positioned directly on surgical instrument 302 and coupled to surgical instrument 302 without any cable. As shown in FIG. 3, connector assembly 306 includes a first RF communication device 312-1 ("first RF device 312-1"), a first induction coil 314-1, and a first light guide 316-1 within a hermetically-sealed housing 318. Connector assembly 306 may include additional or alternative components as may serve a particular implementation. For example, connector assembly 306 may include various electrical signal transmission components (e.g., wires, circuits, optics, etc.).

First RF device 312-1 is disposed within housing 318 and is communicatively coupled to surgical instrument 302 by way of a wired or optical communication link 320. For example, first RF device 312-1 may be mounted or supported on a printed circuit board ("PCB") within housing 318 and electrically coupled to surgical instrument 302 by way of one or more wires. Additionally or alternatively, first RF device 312-1 may be communicatively coupled to surgical instrument 302 by way of one or more optical fibers.

As will be explained below in more detail, when connector assembly 306 is positioned in receiver assembly 308, first RF device 312-1 is configured to align and wirelessly communicate with a second RF communication device 312-2 ("second RF device 312-2") included in receiver assembly 308. First RF device 312-1 may be implemented by any suitable component configured to transmit and/or receive RF signals representative of data. In some examples, first RF device 312-1 may be implemented by a transmitter integrated circuit ("IC") configured to transmit RF signals representative of data generated by surgical instrument 302 (e.g., image data 226). In alternative examples, first RF device 312-1 may be implemented by a receiver IC configured to receive RF signals representative of data generated by controller 304 (e.g., control signals for controlling surgical instrument 302). In additional examples, first RF device 312-1 may be implemented by an RF transceiver configured to both transmit and receive RF signals representative of data.

First induction coil 314-1 is disposed within housing 318 and is electrically coupled to surgical instrument 302 by way of a power wiring 322 (e.g., power wiring 224). First induction coil 314-1 may be implemented by any suitable component that receives wireless power transmission or inductive power transfer. In some examples, first induction coil 314-1 may be implemented by a receiver coil mounted or supported on a PCB or other supporting structure separate from the PCB supporting first RF device 312-1. Alternatively, first induction coil 314-1 may be mounted or supported on the same PCB as first RF device 312-1. As will be explained below in more detail, when connector assembly 306 is positioned in receiver assembly 308, first induction coil 314-1 is configured to inductively couple with a second induction coil 314-2 included in receiver assembly 308 and wirelessly receive electrical power generated by a power source 324 (e.g., power source 220). First induction coil 314-1 may deliver the electrical power to surgical instrument 302 by way of power wiring 322.

First light guide 316-1 is disposed within housing 318 at a proximal end of connector assembly 306 and is optically coupled to surgical instrument 302 by way of an illumination channel 326 (e.g., first illumination channel 214-1 and third illumination channel 214-3). As will be explained below in more detail, when connector assembly 306 is positioned in receiver assembly 308, first light guide 316-1 is configured to align with a second light guide 316-2 in receiver assembly 308 to receive illumination emitted by an illumination source 328 (e.g., illumination source 218) and conveyed by second light guide 316-2. First light guide 316-1 may convey the illumination to surgical instrument 302 by way of illumination channel 326. First light guide 316-1 and illumination channel 326 may each be implemented by one or more optical components (e.g., lenses, optical fibers, light guides, etc.).

Housing 318 covers first RF device 312-1, first induction coil 314-1, and first light guide 316-1 and is hermetically sealed, thereby preventing degradation of all components disposed within housing 318 (e.g., first RF device 312-1, first induction coil 314-1, and first light guide 316-1) when connector assembly 306 undergoes a sterilization process. In some examples, housing 318 may be formed of an electrically non-conductive material, such as plastic.

Housing 318 may be formed to conform to a shape of a receptacle 330 included in receiver assembly 308. In some examples, housing 318 may include a protruding member 332 that protrudes from a front surface 334 of housing 318. As shown in FIG. 3, first light guide 316-1 is disposed within protruding member 332. Protruding member 332 may be formed integrally with housing 318, or it may be a separate element attached to housing 318 and hermetically sealed to housing 318. As will be explained below in more detail, protruding member 332 may be configured to ensure proper alignment of connector assembly 306 when connector assembly 306 is positioned within receiver assembly 308.

Housing 318 further includes a hermetically-sealed window (not shown) at a position optically aligned with first light guide 316-1 to thereby allow light emitted by illumination source 328 to enter first light guide 316-1. In the example shown in FIG. 3, the window may be positioned at a proximal tip end of protruding member 332.

As shown in FIG. 3, first RF device 312-1 and first induction coil 314-1 are positioned within housing 318 on opposite sides of connector assembly 306 to prevent interference with data signals transmitted and/or received by first RF device 312-1, and first light guide 316-1 is positioned at a proximal end of connector assembly 306. However, connector assembly 306 is not limited to this configuration, as first RF device 312-1, first induction coil 314-1, and first light guide 316-1 may be positioned in any suitable location within housing 318, including on the same side or on adjacent sides of connector assembly 306.

As mentioned, connector assembly 306 is configured to be positioned in receiver assembly 308 to communicatively, electrically, and optically couple surgical instrument 302 with controller 304. As shown in FIG. 3, receiver assembly 308 includes second RF device 312-2, second induction coil 314-2, second light guide 316-2, and a receptacle 330. Receiver assembly 308 may include additional or alternative components as may serve a particular implementation. For example, receiver assembly 308 may include various electrical and/or optical signal transmission components (e.g., wires, circuits, optics, etc.).

Second RF device 312-2 is communicatively coupled to controller 304 by way of a communication link 336. For example, second RF device 312-2 may be mounted or supported on a PCB included in receiver assembly 308 and communicatively coupled to a circuit 338 in controller 304 by way of one or more wired or wireless communication links. Additionally or alternatively, second RF device 312-2 may be optically coupled to circuit 338 by way of one or more optical fibers.

Second RF device 312-2 may be implemented by any suitable component configured to transmit and/or receive an RF signal representative of data. In some examples, second RF device 312-2 may be implemented by a receiver IC configured to receive RF signals representative of data generated by surgical instrument 302 (e.g., image data 226). In alternative examples, second RF device 312-2 may be implemented by a transmitter IC configured to transmit RF signals representative of data generated by controller 304 (e.g., control signals for controlling surgical instrument 302). In additional examples, second RF device 312-2 may be implemented by an RF transceiver configured to both transmit and receive RF signals representative of data.

Circuit 338 may include any number of passive or active electrical components (e.g., resistors, capacitors, ICs, coils, etc.) interconnected in any suitable manner so as to perform one or more desired circuit operations. In some examples, circuit 338 may be configured to receive, by way of first RF device 312-1 and second RF device 312-2, signals (e.g., image data 226, kinematic information, etc.) from surgical instrument 302 and generate data (e.g., processed image data 228, kinematic data, etc.) based on the signals. Circuit 338 may further process the data and/or transmit the data to another computing device. In additional or alternative examples, circuit 338 may receive control signals from another component or computing device (e.g., from a computing device included in user control system 104 or auxiliary system 106) and/or generate control signals and transmit, by way of second RF device 312-2 and first RF device 312-1, the control signals to surgical instrument 302. In some examples, circuit 338 may implement CCU 216, an image processor, and/or any other component of surgical system 100 or imaging system 200.

Second induction coil 314-2 is electrically coupled to power source 324 by way of a power wiring 340. Second induction coil 314-2 may be implemented by any suitable component that provides wireless power transmission or inductive power transfer. In some examples, second induction coil 314-2 may be implemented by a transmitter coil mounted or supported on a PCB or other supporting structure separate from the PCB supporting second RF device 312-2. Alternatively, second induction coil 314-2 may be mounted or supported on the same PCB as second RF device 312-2. As will be explained below in more detail, when connector assembly 306 is positioned in receptacle 330, second induction coil 314-2 is configured to inductively couple with first induction coil 314-1 and wirelessly transmit electrical power from power source 324 to surgical instrument 302 by way of first induction coil 314-1.

Although first induction coil 314-1 and second induction coil 314-2 have been described herein as inductively coupling to wirelessly transfer power, any suitable wireless power transmission technology may be used to transfer electrical power from power source 324 to surgical instrument 302. Suitable wireless power transmission technologies include, but are not limited to, resonant inductive coupling, magnetic resonance coupling, capacitive coupling, magnetodynamic coupling, microwave coupling, light wave coupling, and laser coupling.

Second light guide 316-2 is optically coupled to illumination source 328 and configured to receive illumination emitted by illumination source 328 and convey the illumination to receptacle 330. In some examples, second light guide 316-2 may be optically coupled to illumination source 328 by an illumination channel 342. Alternatively, second light guide 316-2 may be optically coupled directly to illumination source 328. Second light guide 316-2 and/or illumination channel 342 may be implemented by one or more optical components (e.g., lenses, optical fibers, light guides, etc.).

Receptacle 330 is configured to receive connector assembly 306 and position connector assembly 306 such that first RF device 312-1 is aligned with second RF device 312-2, first induction coil 314-1 is aligned with second induction coil 314-2, and first light guide 316-1 is optically aligned with second light guide 316-2. To this end, receptacle 330 includes a sheath 344, a hollow portion 346 defined by an interior surface of sheath 344, and an opening 348 that allows insertion of connector assembly 306 into receptacle 330. Sheath 344 may be formed to conform to a shape of an external surface of housing 318, such that sheath 344 supports connector assembly 306 when connector assembly 306 is positioned in receptacle 330. In some examples, sheath 344 may be formed of an electrically non-conductive material, such as a plastic.

In some examples in which connector assembly 306 includes protruding member 332, receptacle 330 may also include a recess 350 formed in sheath 344 to receive protruding member 332 when connector assembly 306 is positioned in receptacle 330. Second light guide 316-2 may be positioned in receiver assembly 308 adjacent to recess 350 such that second light guide 316-2 aligns with first light guide 316-1 when connector assembly 306 is positioned in receptacle 330. In some examples, sheath 344 may be formed such that recess 350 and protruding member 332 function as an alignment mechanism to ensure proper alignment of connector assembly 306 when connector assembly 306 is positioned in receptacle 330.

As shown in FIG. 3, second RF device 312-2, second induction coil 314-2, and second light guide 316-2 are positioned in receiver assembly 308 outside of receptacle 330 (e.g., adjacent to or facing an external surface of sheath 344). In some examples, second RF device 312-2 and/or second induction coil may be mounted on an external surface of sheath 344. Alternatively, second RF device 312-2 and/or second induction coil 314-2 may be mounted on one or more separate PCBs or other supporting structures positioned adjacent to sheath 344.

As shown in FIG. 3, second RF device 312-2 and second induction coil 314-2 are positioned on opposite sides of sheath 344 to prevent interference with data signals transmitted and/or received by second RF device 312-2, and second light guide 316-2 is positioned at a distal end of receptacle 330. However, receiver assembly 308 is not limited to this configuration, as second RF device 312-2, second induction coil 314-2, and second light guide 316-2 may be positioned in any suitable location, including on the same side or on adjacent sides of sheath 344.

Figure 4:
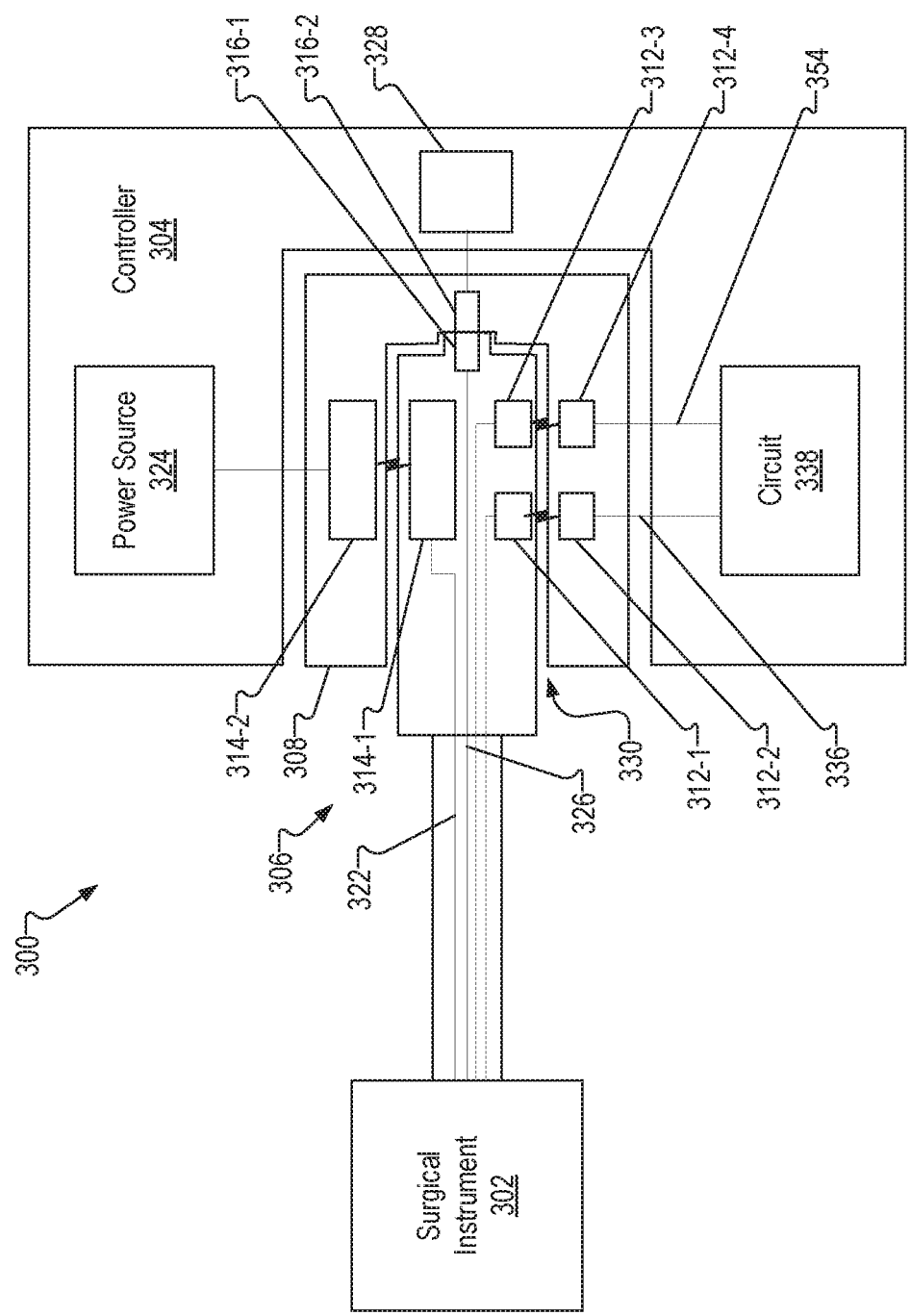
FIG. 4 illustrates another functional diagram of the exemplary connection system of FIG. 3 according to principles described herein.

FIG. 4 illustrates connection system 300 in which connector assembly 306 is positioned in receiver assembly 308 (e.g., in receptacle 330). As shown, first RF device 312-1 is aligned with second RF device 312-2 such that RF signals transmitted by first RF device 312-1 are received by second RF device 312-2 and transmitted to controller 304 by way of communication link 336. In this way first RF device 312-1 may wirelessly communicate with second RF device 312-2 and thereby enable communication between surgical instrument 302 and controller 304 (e.g., circuit 338). Similarly, second induction coil 314-2 is aligned with first induction coil 314-1 such that second induction coil 314-2 inductively couples to first induction coil 314-1. In this way, second induction coil 314-2 may wirelessly transmit electrical power provided by power source 324 to first induction coil 314-1, which delivers the electrical power to surgical instrument 302 by way of power wiring 322. Additionally, first light guide 316-1 is aligned with second light guide 316-2 such that light emitted from illumination source 328 is conveyed by second light guide 316-2 to first light guide 316-1. The received light is then conveyed by first light guide 316-1 to surgical instrument 302 (e.g., an endoscope) by way of illumination channel 326 and exits surgical instrument 302 to illuminate a scene.

To facilitate alignment of connector assembly 306 in receptacle 330, connector assembly 306 (e.g., housing 318) and receptacle 330 (e.g., sheath 344) may include any suitable structures or mechanisms, such as but not limited to a notch, a protrusion, a groove, a recess, a snap, a guide, etc.

Connection system 300 of FIGS. 3 and 4 may include any number of communication, power, and/or optical channels as may suit a particular implementation. For instance, first RF device 312-1 and second RF device 312-2 may be configured to operate only unidirectionally. For example, connection system 300 may provide a first communication channel dedicated for transmitting data from surgical instrument 302 to controller 304 and a second communication channel dedicated for transmitting data from controller 304 to surgical instrument 302. Alternatively, the second communication channel may be dedicated for transmitting data from surgical instrument 302 to controller 304.

An exemplary second communication channel will now be described. As shown in FIGS. 3 and 4, connector assembly 306 includes a third RF communication device 312-3 ("third RF device 312-3") communicatively coupled with surgical instrument 302 by way of communication link 352. Third RF device 312-3 may be coupled with surgical instrument 302 in any suitable manner. Receiver assembly 308 may include a fourth RF communication device 312-4 ("fourth RF device 312-4") communicatively coupled with controller 304 by way of communication link 354. Fourth RF device 312-4 may be coupled with controller 304 in any suitable manner. As shown in FIG. 4, when connector assembly 306 is positioned in receptacle 330, third RF device 312-3 is aligned with fourth RF device 312-4 such that third RF device 312-3 is configured to wirelessly communicate with fourth RF device 312-4.

In some examples, first RF device 312-1 is implemented as a transmitter IC configured to transmit RF signals representative of data generated by surgical instrument 302 and second RF device 312-2 is implemented as a receiver IC configured to receive the RF signals transmitted by first RF device 312-1, while fourth RF device 312-4 is implemented as a transmitter IC configured to transmit RF signals representative of data generated by controller 304 and third RF device 312-3 is implemented as a receiver IC configured to receive the RF signals transmitted by fourth RF device 312-4. Thus, first RF device 312-1 and second RF device 312-2 are formed in a first communication channel dedicated for transmitting data (e.g., image data 226) from surgical instrument 302 to controller 304, and third RF device 312-3 and fourth RF device 312-4 are formed in a second communication channel dedicated for transmitting data (e.g., control signals) from controller 304 to surgical instrument 302.

In additional examples, first RF device 312-1 and third RF device 312-3 are implemented as transmitter ICs and second RF device 312-2 and fourth RF device 312-4 are implemented as receiver ICs. When connector assembly 306 is positioned in receptacle 330, first RF device 312-1 and third RF device 312-3 are configured to wirelessly transmit data generated by surgical instrument 302 to controller 304 by way of second RF device 312-2 and fourth RF device 312-4, respectively. Where surgical instrument 302 is implemented by a stereoscopic endoscope, such a configuration may facilitate high-speed transmission of stereoscopic image data from surgical instrument 302 to controller 304.

To illustrate, surgical instrument 302 may be implemented by imaging device 202 and controller 304 may be implemented by controller 204. First RF device 312-1 and second RF device 312-2 may be formed in a first communication channel configured to transmit image data 226-L from image sensor 212-L to CCU 216 of controller 204. Similarly, third RF device 312-3 and fourth RF device 312-4 may be formed in a second communication channel configured to transmit image data 226-R from image sensor 212-R to CCU 216.

In some examples, RF devices 312 may be implemented by ICs configured to transmit and/or receive RF signals in the extremely high frequency ("EHF") range (i.e., 30-300 gigahertz ("GHz")). For instance, RF devices 312 may be implemented by or similar to transmitter and receiver ICs manufactured by KEYSSA, INC. (Campbell, California). Such transmitter and receiver ICs are designed to transmit and receive data when in direct RF signal path alignment with each other. For example, a transmitter IC similar to transmitter ICs manufactured by KEYSSA is configured to emit RF signals in a direction that is orthogonal to a top surface of the transmitter IC. Similarly, a receiver IC similar to receiver ICs manufactured by KEYSSA is configured to receive RF signals that are orthogonal to a top surface of the receiver IC. Accordingly, first RF device 312-1 and second RF device 312-2 may be configured such that a top surface of first RF device 312-1 is substantially parallel to a top surface of second RF device 312-2, Similarly, third RF device 312-3 and fourth RF device 312-4 may be configured such that a top surface of third RF device 312-3 is substantially parallel to a top surface of fourth RF device 312-4.

In some examples first RF device 312-1 and third RF device 312-3 may be mounted on a first PCB, or may otherwise be positioned near each other within connector assembly 306. Similarly, second RF device 312-2 and fourth RF device 312-4 may be mounted on a second PCB, or may otherwise be positioned near each other within receiver assembly 308. To prevent cross-talk and/or interference with the communication channels, RF devices 312 may be shielded with an RF absorber or other material configured to shield each RF device 312 from stray RF signals.

Figure 5A:
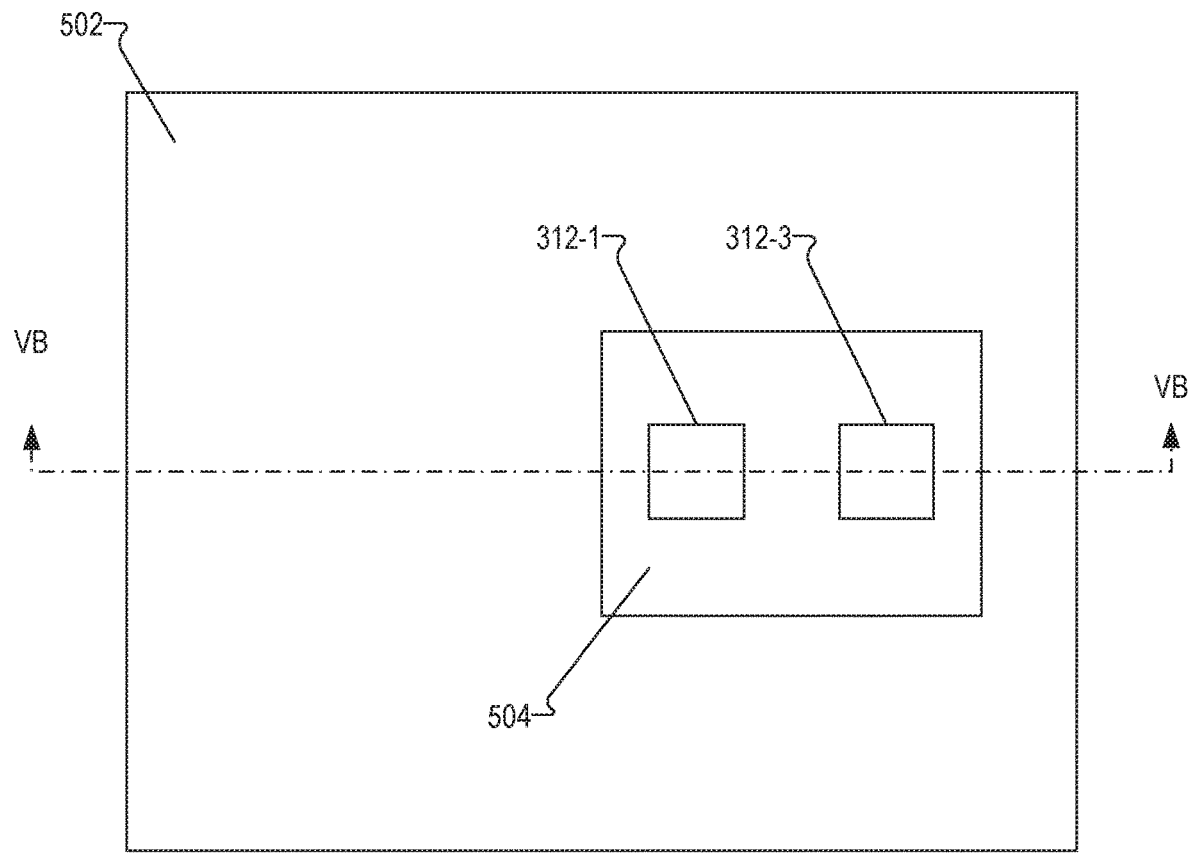
FIG. 5A illustrates a plan view of an exemplary configuration of a first RF communication device and a third RF communication device included in a connector assembly according to principles described herein.
Figure 5B:
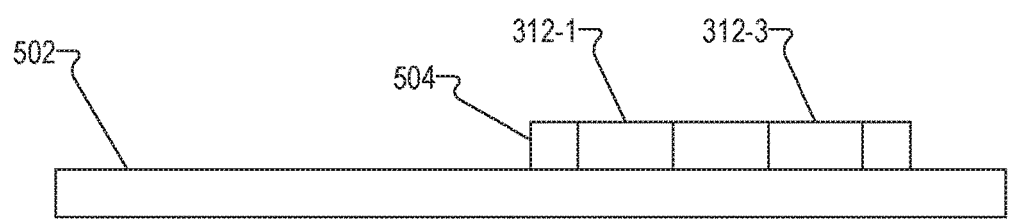
FIG. 5B illustrates a cross-sectional view of FIG. 5A taken along the line labeled VB-VB according to principles described herein.

For example, FIG. 5A illustrates a plan view of an exemplary configuration of first RF device 312-1 and third RF device 312-3 for reducing or preventing cross-talk and interference. FIG. 5B illustrates a cross-sectional view of the configuration shown in FIG. 5A, taken along the line labeled VB-VB. As shown in FIGS. 5A and 5B, first RF device 312-1 and third RF device 312-3 may be mounted on a first PCB 502. First PCB 502 may also include any other components as may suit a particular implementation. However, for purposes of this discussion only first RF device 312-1 and third RF device 312-3 are shown. A first RF absorber plate 504 is disposed on first PCB 502 surrounding side edges of first RF device 312-1 and third RF device 312-3. As shown in FIG. 5B, first RF absorber plate 504 is coplanar with top surfaces of first RF device 312-1 and third RF device 312-3. However, first RF absorber plate 504 is not limited to this configuration, and may be thicker or thinner than first RF device 312-1 and third RF device 312-3, as may suit a particular implementation.

Figure 6A:
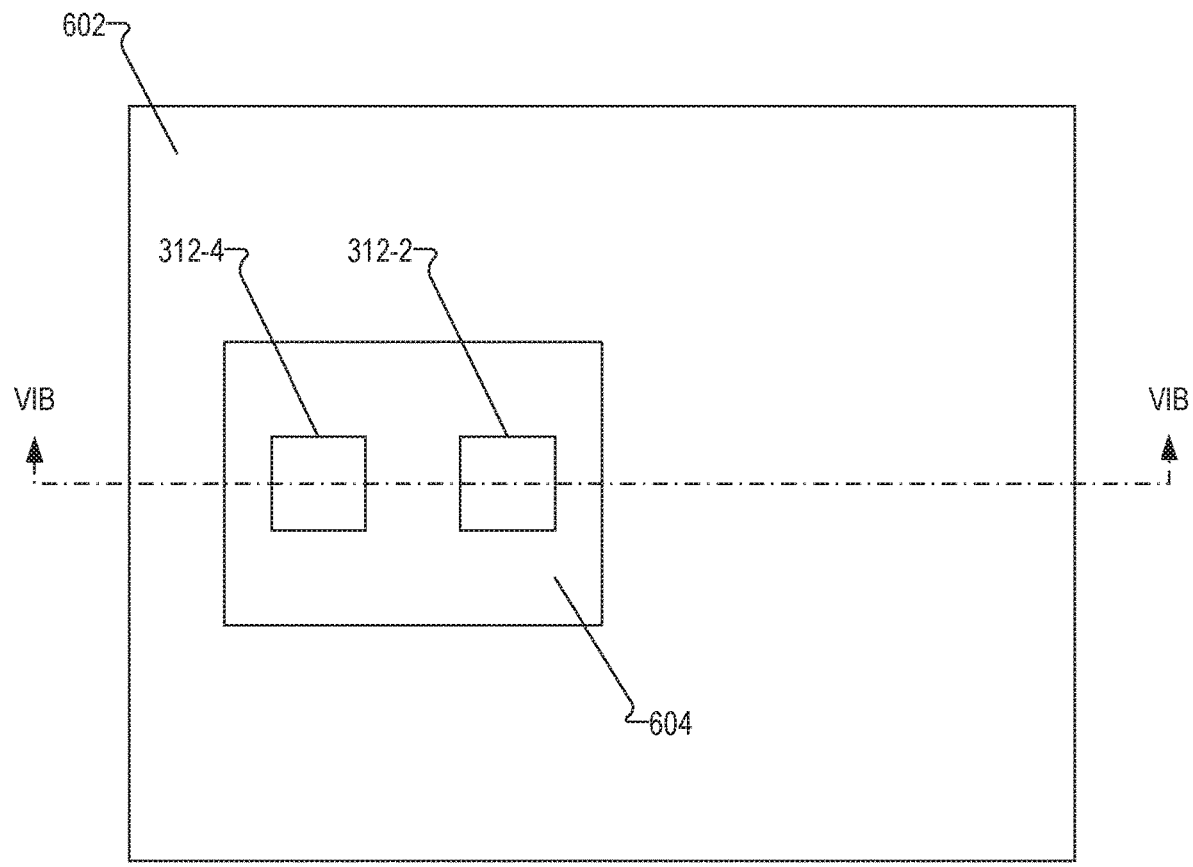
FIG. 6A illustrates a plan view of an exemplary configuration of a second RF communication device and a fourth RF communication device included in a receiver assembly according to principles described herein.
Figure 6B:
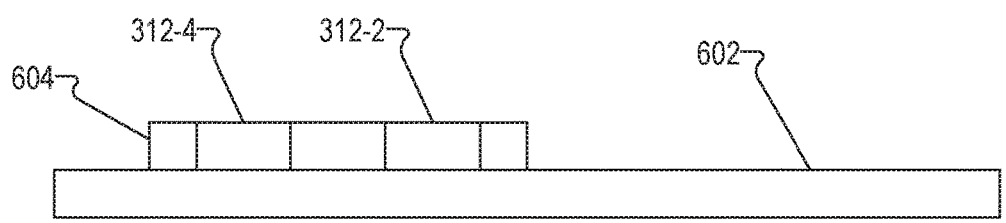
FIG. 6B illustrates a cross-sectional view of FIG. 6A taken along the line labeled VIB-VIB according to principles described herein.

Similarly, FIG. 6A illustrates a plan view of an exemplary configuration of second RF device 312-2 and fourth RF device 312-4 for reducing or preventing cross-talk and interference. FIG. 6B illustrates a cross-sectional view of the configuration shown in FIG. 6A, taken along the line labeled VIB-VIB. As shown in FIGS. 6A and 6B, second RF device 312-2 and fourth RF device 312-4 may be mounted on a second PCB 602. Second PCB 602 may also include any other components as may suit a particular implementation. However, for purposes of this discussion only second RF device 312-2 and fourth RF device 312-4 are shown. A second RF absorber plate 604 is disposed on second PCB 602 surrounding side edges of second RF device 312-2 and fourth RF device 312-4. As shown in FIG. 6B, second RF absorber plate 604 is coplanar with top surfaces of second RF device 312-2 and fourth RF device 312-4. However, second RF absorber plate 604 is not limited to this configuration, and may be thicker or thinner than second RF device 312-2 and fourth RF device 312-4, as may suit a particular implementation.

First RF absorber plate 504 and second RF absorber plate 604 may be implemented by any suitable component configured to absorb or shield RF signals, including but not limited to a foam absorber, a rubber absorber, and the like.

Referring again to FIGS. 3 and 4, connection system 300 may include any number of communication, power, and/or optical channels as may suit a particular implementation. For example, connection system 300 does not include any optical channels. For instance, where surgical instrument 302 is not an imaging device and does not require illumination, connector assembly 306 does not include first light guide 316-1 or illumination channel 326. However, receiver assembly 308 may optionally still include second light guide 316-2 and illumination channel 342 to allow an endoscope or other imaging device to later be coupled to controller 304 via receiver assembly 308.

Additionally, although the communication channels in connection system 300 have been described as being implemented by wired and RF communication, the communication channels may alternatively be implemented by an optical communication channel. For example, first light guide 316-1 and second light guide 316-2 may be configured to convey optical signals representative of data between surgical instrument 302 and controller 304. Accordingly, connection system 300 and/or controller 304 may include various optical signal transmission components (e.g., lenses, optical fibers, light guides, filters, etc.).

Furthermore, although FIGS. 3 and 4 show that connector assembly 306 is coupled to surgical instrument 302 by way of cable 310, connection system 300 is not limited to this arrangement. For example, connector assembly 306 may be coupled to controller 304 and receiver assembly 308 may be coupled to surgical instrument 302.

Figure 7A:
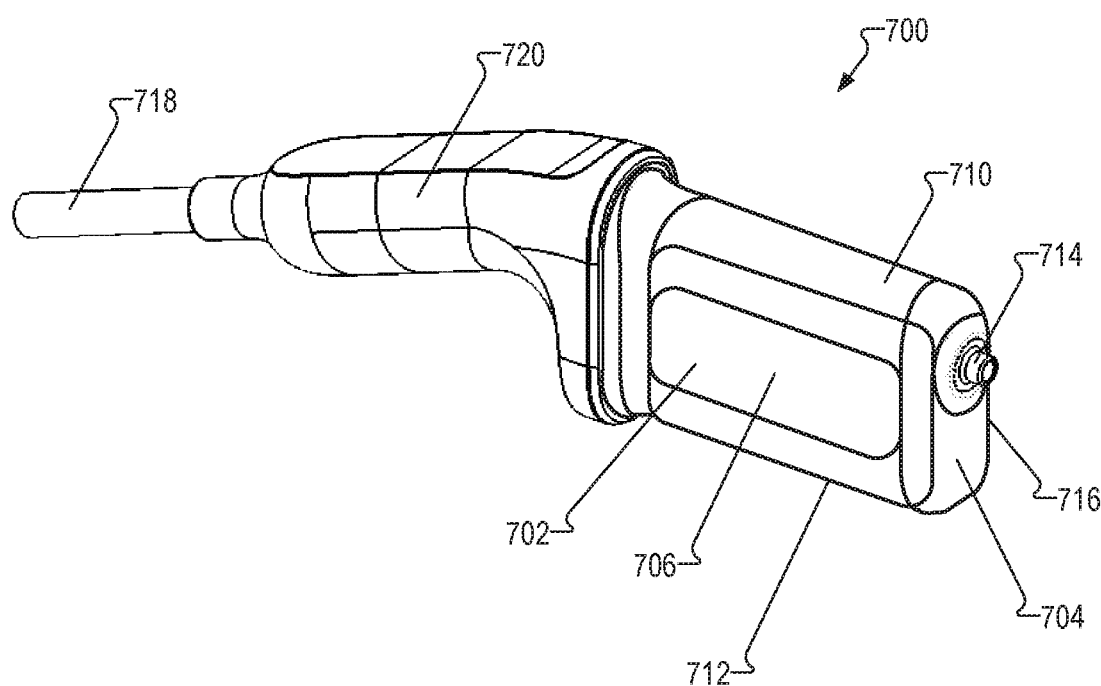
FIGS. 7A and 7B illustrate perspective views of an exemplary connector assembly according to principles described herein.
Figure 7B:
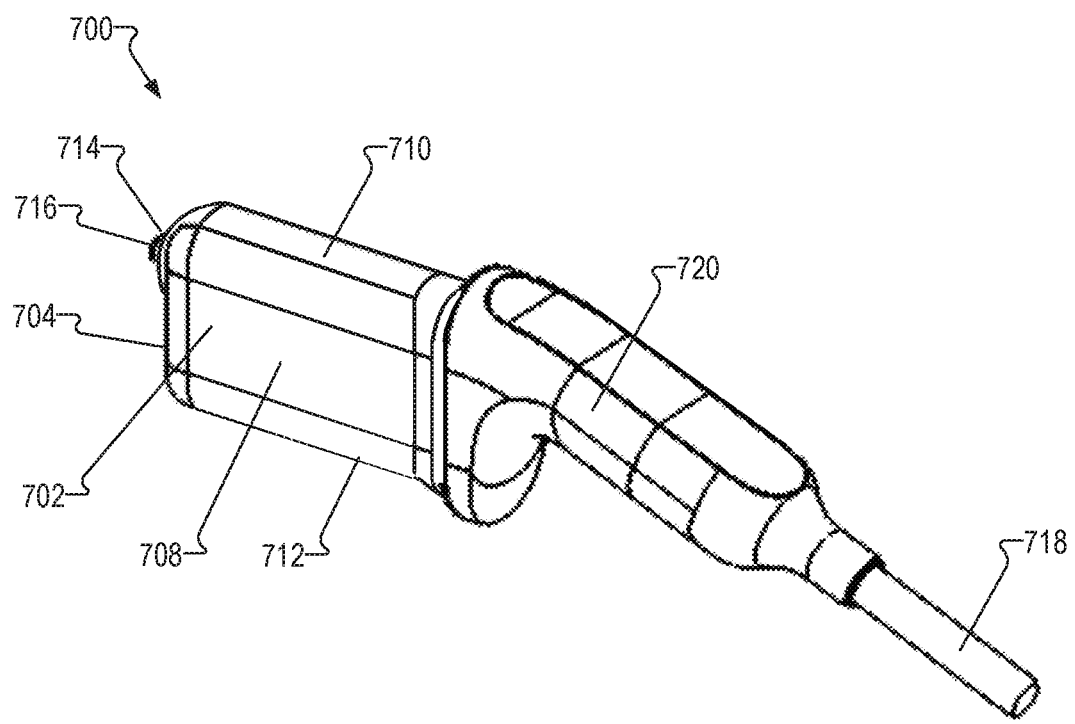

FIGS. 7A and 7B illustrate perspective views of an exemplary connector assembly 700 that implements connector assembly 306. Connector assembly 700 includes a hermetically sealed housing 702 that houses a first RF communication device, a first induction coil, and a first light guide (not shown in FIGS. 7A and 7B). Housing 702 includes a front surface 704 (e.g., a surface at a proximal end connector assembly 700), a first side surface 706, a second side surface 708 positioned opposite to first side surface 706, a top surface 710, and a bottom surface 712 positioned opposite to top surface 710. Housing 702 further includes a protruding member 714 that protrudes from front surface 704 and a window 716 positioned at the proximal tip end of protruding member 714. The first RF communication device may be positioned on or adjacent to first side surface 706 and the first induction coil may be positioned on or adjacent to second side surface 708.

A proximal end of a cable 718 is connected to a distal end of connector assembly 700, and a distal end of cable 718 may be connected to a surgical instrument (not shown in FIGS. 7A and 7B). In some examples, as shown in FIGS. 7A and 7B, connector assembly 700 may further include a handle 720 configured to facilitate user handling of connector assembly 700 and to protect the connection of cable 718 to connector assembly 700.

Figure 8A:
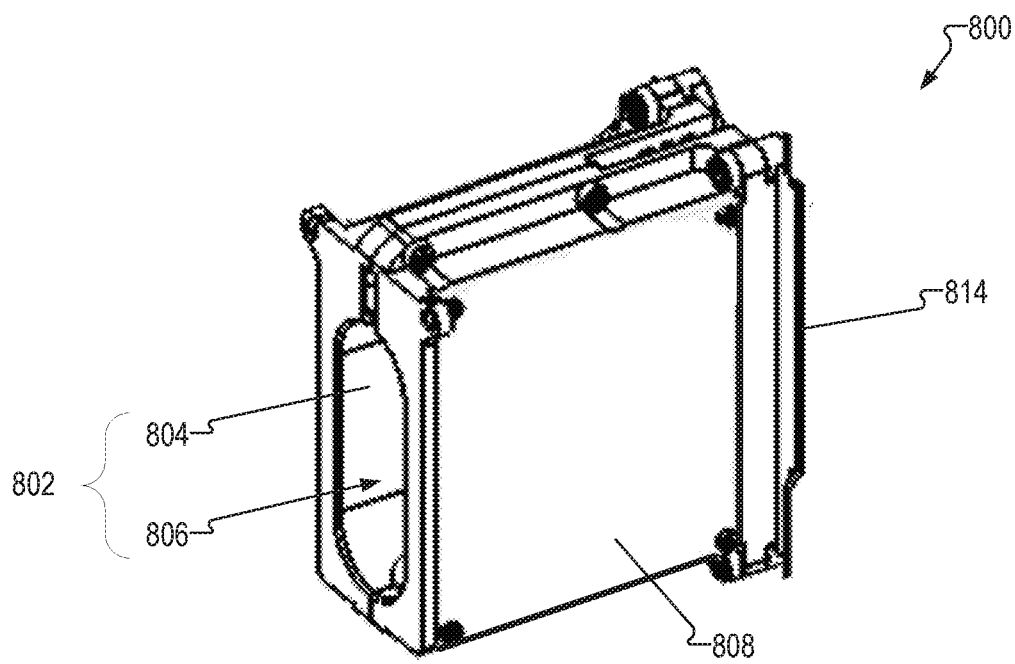
FIGS. 8A and 8B illustrate perspective views of an exemplary receiver assembly according to principles described herein.
Figure 8B:
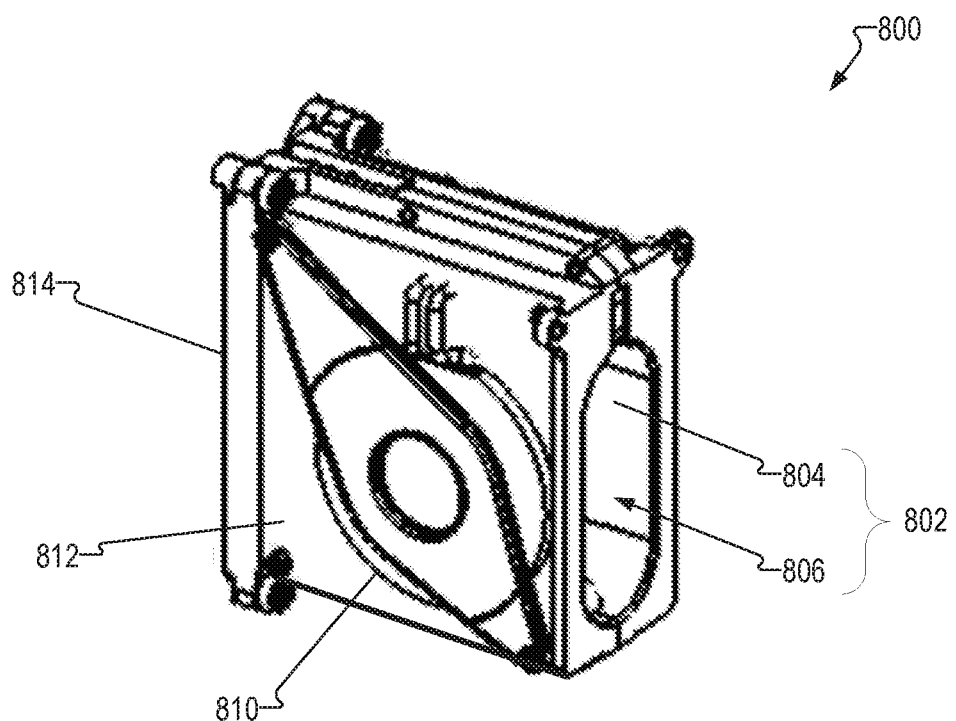

FIGS. 8A and 8B illustrate perspective views of an exemplary receiver assembly 800 that implements receiver assembly 308 configured to receive connector assembly 700. As shown, receiver assembly 800 includes a receptacle 802 formed by a sheath 804 and a hollow portion 806 inside of sheath 804. A second RF communication device (not shown) is mounted on a first PCB 808 facing sheath 804 on a first side (e.g., a right side) of sheath 804. The second RF communication device may be communicatively coupled to a controller of a surgical instrument. A second induction coil 810 is mounted on a second PCB 812 facing sheath 804 on a second side (e.g., a left side) of sheath 804 and is electrically coupled to a power source. A second light guide (not shown) is positioned adjacent to a back side surface 814 of sheath 804 and is optically coupled to an illumination source.

As shown in FIGS. 7A and 7B, connector assembly 700 does not have any exposed conductive contacts (e.g., leads, pins, prongs). Similarly, as shown in FIGS. 8A and 8B, receiver assembly 800 does not have any conductive contacts (e.g., leads, pins, prongs) that are exposed to connector assembly 700. Therefore, connector assembly 700 and receiver assembly 800 do not make conductive contact when connector assembly 700 is positioned in receiver assembly 800. Additionally, since housing 702 of connector assembly 700 is hermetically sealed, connector assembly 700 can be sterilized and cleansed without degrading internal components of connector assembly 700 (e.g., the first RF communication device, first induction coil, first light guide, etc.).

In some examples a connector assembly and a receiver assembly may be configured to provide multiface channels that enable power transmission, data communication, and optical transmission across different faces or surfaces of the connector assembly and the receiver assembly. For example, while connector assembly 700 is positioned in receiver assembly 800, the first RF communication device in connector assembly 700 may be configured to wirelessly communicate with the second RF communication device in receiver assembly 800 across a first face of connector assembly 700 (e.g., first side surface 706 of housing 702) and a first face of receiver assembly 800 (e.g., a right-side surface of sheath 804 adjacent to first PCB 808). In this way connector assembly 700 and receiver assembly 800 may form a data communication channel across the first face of connector assembly 700 and the first face of receiver assembly 800.

Additionally, while connector assembly 700 is positioned in receiver assembly 800, second induction coil 810 in receiver assembly 800 may be configured to inductively couple to the first induction coil in connector assembly 700 across a second face of connector assembly 700 (e.g., second side surface 708 of housing 702) and a second face of receiver assembly 800 (e.g., a left-side face of sheath 804 adjacent to second PCB 812). In this way connector assembly 700 and receiver assembly 800 may form a power transmission channel across the second face of connector assembly 700 and the second face of receiver assembly 800.

Additionally, while connector assembly 700 is positioned in receiver assembly 800, the first light guide in connector assembly 700 may be optically aligned with the second light guide in receiver assembly 800 such that light is conveyed across a third face of receiver assembly 800 (e.g., back side surface 814 of sheath 804) and a third face of connector assembly 700 (e.g., front surface 704 of housing 702) by way of the second light guide and the first light guide. In this way connector assembly 700 and receiver assembly 800 may form an optical channel across the third face of connector assembly 700 and the third face of receiver assembly 800.

A multiface channel configuration of the connector assembly and the receiver assembly enables a data communication channel, power transmission channel, and optical channel to be provided in the connector assembly and receiver assembly in a compact form, thus reducing the size of the connector assembly and the receiver assembly. At the same time, the multiface channel configuration may reduce or even prevent interference between the power channel and the data channel.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:
1. A system comprising:
a connector assembly comprising:
   a hermetically-sealed housing including a first side surface, a second side surface positioned opposite to the first side surface, and a third side surface that intersects with at least one of the first side surface or the second side surface,
   a first radio frequency ("RF") communication device disposed within the housing and communicatively coupled to a surgical instrument,
   a first induction coil disposed within the housing and electrically coupled to the surgical instrument, and
   a first light guide disposed within the housing and optically coupled to the surgical instrument, and
a receiver assembly comprising:
   a second RF communication device communicatively coupled to a controller of the surgical instrument,
   a second induction coil electrically coupled to a power source,
   a second light guide optically coupled to an illumination source configured to emit illumination light, and
   a receptacle configured to receive the connector assembly such that, while the connector assembly is positioned in the receptacle, the first RF communication device is aligned with the second RF communication device, the first induction coil is aligned with the second induction coil, and the first light guide is optically aligned with the second light guide,
wherein, while the connector assembly is positioned in the receptacle, the first RF communication device is configured to wirelessly communicate with the second RF communication device across the first side surface, the second induction coil is configured to inductively couple to the first induction coil to wirelessly transmit power to the surgical instrument across the second side surface by way of the first induction coil, and the illumination light emitted from the illumination source is conveyed by the second light guide across the third side surface to the surgical instrument by way of the first light guide.

2. The system of claim 1, wherein the housing includes a hermetically-sealed window at a position optically aligned with the first light guide.

3. The system of claim 1, wherein
the housing includes a protruding member that protrudes from a front surface of the housing,
the first light guide is disposed within the protruding member,
the receptacle includes a recess portion configured to receive the protruding member, and
the second light guide is disposed adjacent to the recess portion.

4. The system of claim 3, wherein, while the connector assembly is positioned in the receptacle, the protruding member and the recess portion are configured to maintain the first light guide in optical alignment with the second light guide.

5. The system of claim 1, wherein the first RF communication device is configured to wirelessly transmit data generated by the surgical instrument to the controller by way of the second RF communication device while the connector assembly is positioned in the receptacle.

6. The system of claim 1, wherein the second RF communication device is configured to receive control signals from the controller and wirelessly transmit the control signals to the surgical instrument by way of the first RF communication device.

7. The system of claim 1, wherein:
the connector assembly further comprises a third RF communication device disposed within the housing and communicatively coupled to the surgical instrument,
the receiver assembly further comprises a fourth RF communication device communicatively coupled to the controller, and
while the connector assembly is positioned in the receptacle,
the third RF communication device is aligned with the fourth RF communication device, and
the third RF communication device is configured to wirelessly communicate with the fourth RF communication device.

8. The system of claim 7, wherein
the surgical instrument comprises a stereoscopic imaging device configured to generate left image data and right image data,
the first RF communication device is configured to wirelessly transmit the left image data to the controller by way of the second RF communication device, and
the third RF communication device is configured to wirelessly transmit the right image data to the controller by way of the fourth RF communication device.

9. The system of claim 7, wherein
the first RF communication device and the third RF communication device are disposed on a first printed circuit board ("PCB"), and a first absorber plate is disposed on the first PCB surrounding side surfaces of the first RF communication device and the third RF communication device.

10. The system of claim 9, wherein
the second RF communication device and the fourth RF communication device are disposed on a second PCB, and
a second absorber plate is disposed on the second PCB surrounding side surfaces of the second RF communication device and the fourth RF communication device.

11. The system of claim 1, wherein
the surgical instrument comprises an endoscope,
the controller includes at least one of a camera control unit and an image processor,
the second RF communication device is communicatively coupled to the at least one of the camera control unit and the image processor, and
the first RF communication device is configured to wirelessly transmit image data generated by the endoscope to the at least one of the camera control unit and the image processor by way of the second RF communication device.

12. The system of claim 1, wherein
the first RF communication device comprises a transmitter integrated circuit ("IC") configured to transmit RF signals in an extremely high frequency ("EHF") range, and
the second RF communication device comprises a receiver IC configured to receive RF signals in the EHF range.

13. The system of claim 1, wherein, while the connector assembly is positioned in the receptacle, a top surface of the first RF communication device is substantially parallel to a top surface of the second RF communication device.

14. The system of claim 1, wherein
the first RF communication device comprises an RF transmitter, and
the second RF communication device comprises an RF receiver.

15. The system of claim 1, wherein the first RF communication device and the second RF communication device comprise RF transceivers.

16. A connector assembly comprising:
a hermetically-sealed housing including a first side surface, a second side surface positioned opposite to the first side surface, and a third side surface that intersects with at least one of the first side surface or the second side surface;
a first radio frequency ("RF") communication device disposed within the housing and communicatively coupled to a surgical instrument;
a first induction coil electrically coupled to the surgical instrument; and
a first light guide disposed within the housing and optically coupled to the surgical instrument;
wherein the connector assembly is configured to be positioned in a receptacle of a receiver assembly such that, while the connector assembly is positioned in the receptacle,
the first RF communication device is aligned with a second RF communication device included in the receiver assembly,
the first induction coil is aligned with a second induction coil included in the receiver assembly, the second induction coil being electrically coupled to a power source, and the first light guide is optically aligned with a second light guide included in the receiver assembly, the second light guide being optically coupled to an illumination source configured to emit illumination light; and wherein, while the connector assembly is positioned in the receptacle,
- the first RF communication device is configured to wirelessly communicate with the second RF communication device across the first side surface,
- the second induction coil is configured to inductively couple to the first induction coil to wirelessly transmit power to the surgical instrument across the second side surface by way of the first induction coil, and
- the illumination light emitted from the illumination source is conveyed by the second light guide across the third side surface to the surgical instrument by way of the first light guide.

* * * * *